United States Patent
Claypool et al.

(10) Patent No.: US 10,166,034 B2
(45) Date of Patent: Jan. 1, 2019

(54) KNEE ARTHROPLASTY INSTRUMENT

(75) Inventors: Jody L. Claypool, Warsaw, IN (US);
Joshin Sahadevan, Warsaw, IN (US);
Siddhi Vinayak, Warsaw, IN (US);
Steven E. Stump, Goshen, IN (US)

(73) Assignee: Zimmer, Inc., Warsaw, IN (US)

( * ) Notice: Subject to any disclaimer, the term of this patent is extended or adjusted under 35 U.S.C. 154(b) by 1307 days.

(21) Appl. No.: 14/233,227

(22) PCT Filed: Jul. 19, 2012

(86) PCT No.: PCT/US2012/047479
§ 371 (c)(1),
(2), (4) Date: May 1, 2014

(87) PCT Pub. No.: WO2013/013094
PCT Pub. Date: Jan. 24, 2013

(65) Prior Publication Data
US 2014/0288563 A1   Sep. 25, 2014

Related U.S. Application Data

(60) Provisional application No. 61/509,355, filed on Jul. 19, 2011.

(51) Int. Cl.
| | |
|---|---|
| *A61B 17/15* | (2006.01) |
| *A61B 17/17* | (2006.01) |
| *A61B 17/56* | (2006.01) |
| *A61B 17/02* | (2006.01) |
| *A61B 90/00* | (2016.01) |

(52) U.S. Cl.
CPC ........ *A61B 17/1764* (2013.01); *A61B 17/025* (2013.01); *A61B 17/155* (2013.01);
(Continued)

(58) Field of Classification Search
CPC ............... A61B 17/1764; A61B 17/88; A61B 2/4657–2002/4668
See application file for complete search history.

(56) References Cited

U.S. PATENT DOCUMENTS 5,860,980 A * 1/1999 Axelson, Jr. ......... A61B 17/155
606/88
6,056,756 A * 5/2000 Eng ..................... A61B 17/155
606/87

(Continued)

FOREIGN PATENT DOCUMENTS

| CN | 107106189 | 8/2017 |
| FR | 2949315 A1 | 4/2011 |

(Continued)

OTHER PUBLICATIONS

"U.S. Appl. No. 14/880,522, Restriction Requirement dated Oct. 20, 2017", 6 pgs.
(Continued)

*Primary Examiner* — Zade Coley
(74) *Attorney, Agent, or Firm* — Schwegman Lundberg & Woessner, P.A.

(57) ABSTRACT

An instrument (10) and method are provided for total knee arthroplasty (TKA). The instrument separates a patient's tibia and femur, in both extension and flexion, to measure a gap and an angle therebetween. The instrument includes various modular accessories (16, 54, 70, 80, 90, 100) that provide flexibility of usage throughout the TKA procedure and that accommodate different surgical philosophies.

15 Claims, 15 Drawing Sheets

(52) U.S. Cl.
CPC ............... *A61B 2017/0268* (2013.01); *A61B 2090/061* (2016.02); *A61B 2090/067* (2016.02)

(56) References Cited

U.S. PATENT DOCUMENTS

| | | | |
|---|---|---|---|
| 7,156,853 B2 * | 1/2007 | Muratsu | A61B 17/0206 606/102 |
| 9,050,197 B2 | 6/2015 | Lorio et al. | |
| 2004/0122441 A1 | 6/2004 | Muratsu | |
| 2005/0256527 A1 | 11/2005 | Delfosse et al. | |
| 2007/0173851 A1 * | 7/2007 | McMillen | A61B 17/1764 606/87 |
| 2007/0293868 A1 * | 12/2007 | Delfosse | A61B 17/025 606/88 |
| 2009/0138021 A1 | 5/2009 | Colquhoun et al. | |
| 2011/0046685 A1 * | 2/2011 | Faure | A61B 17/155 606/86 R |
| 2013/0144302 A1 | 6/2013 | Reeve | |
| 2014/0025081 A1 | 1/2014 | Lorio et al. | |
| 2014/0228853 A1 | 8/2014 | Rock | |
| 2016/0135825 A1 | 5/2016 | Toler | |

FOREIGN PATENT DOCUMENTS

| | | | | |
|---|---|---|---|---|
| JP | 8229058 A | 9/1996 | | |
| JP | 11113940 A | 4/1999 | | |
| JP | 2001517135 A | 10/2001 | | |
| JP | 2004237064 A | 8/2004 | | |
| JP | 2014524815 A | 9/2014 | | |
| JP | 6055825 | 12/2016 | | |
| WO | WO 0185038 A1 * | 11/2001 | ......... | A61B 17/155 |
| WO | WO-0185038 A1 | 11/2001 | | |
| WO | WO-200185038 A1 | 11/2001 | | |
| WO | WO-2007036694 A1 | 4/2007 | | |
| WO | WO-2013013094 A1 | 1/2013 | | |
| WO | WO-2014006360 A1 | 1/2014 | | |
| WO | WO-2016081094 A1 | 5/2016 | | |

OTHER PUBLICATIONS

"International Application Serial No. PCT/US2015/055087, International Preliminary Report on Patentability dated Jun. 1, 2017", 9 pgs.

"U.S. Appl. No. 14/880,522, Response filed Dec. 19, 2017 to Restriction Requirement dated Oct. 20, 2017", 8 pgs.

"International Application Serial No. PCT/US2012/047479, Search Report dated Sep. 10, 2012", 10 pgs.

"International Application Serial No. PCT/US2012/047479, Written Opinion dated Sep. 10, 2012", 7 pgs.

"International Application Serial No. PCT/US2012/047479, International Preliminary Report on Patentability dated Jan. 30, 2014", 9 pgs.

"Attune Surgical Technique", DePuy Orthopaedics Inc., (2012), 31 pgs.

"European Application Serial No. 12741216.1, Communication Pursuant to Article 94(3) EPC dated Jan. 8, 2016", 6 pgs.

"European Application Serial No. 12741216.1, Response filed Jul. 18, 2016 to Communication Pursuant to Article 94(3) EPC dated Jan. 8, 2016", 15 pgs.

"European Application Serial No. 12741216.1, Response filed Sep. 29, 2014 to Communication pursuant to Rules 161(1) and 162 EPC dated Mar. 19, 2014", 14 pgs.

"Flexion/Extension Gap Balancing Surgical Technique Addendum", Smith & Nephew Journey BCS Bi-Cruciate Stabilized Knee System, (Jan. 2008), 4 pgs.

"international Application Serial No. PCT/US2015/055087, International Search Report dated Jan. 21, 2016", 7 pgs.

"International Application Serial No. PCT/US2015/055087, Written Opinion dated Jan. 21, 2016", 7 pgs.

"Japanese Application Serial No. 2014-521804, Amendment filed Jun. 23, 2015", (W/ English Translation), 7 pgs.

"Japanese Application Serial No. 2014-521804, Office Action dated Jul 5, 2016", (W/ English Translation), 8 pgs.

"Japanese Application Serial No. 2014-521804, Response filed Sep. 13, 2016 to Office Action dated Jul. 5, 2016", (English Translation of Claims), 17 pgs.

"Triathlon Knee System Gap Balancing Technique Surgical Protocol Addendum", Stryker Orthopaedics, Literature No. LSPK55, (2010), 8 pgs.

"U.S. Appl. No. 14/880,522, Non Final Office Action dated Jan. 16, 2018", 11 pgs.

"U.S. Appl. No. 14/880,522, Response filed Mar. 30, 2018 to Non Final Office Action dated Jan. 16, 2018", 11 pgs.

"European Application Serial No. 15790721.3, Response filed Feb. 12, 2018 to Action dated Aug. 1, 2017", 13 pgs.

* cited by examiner

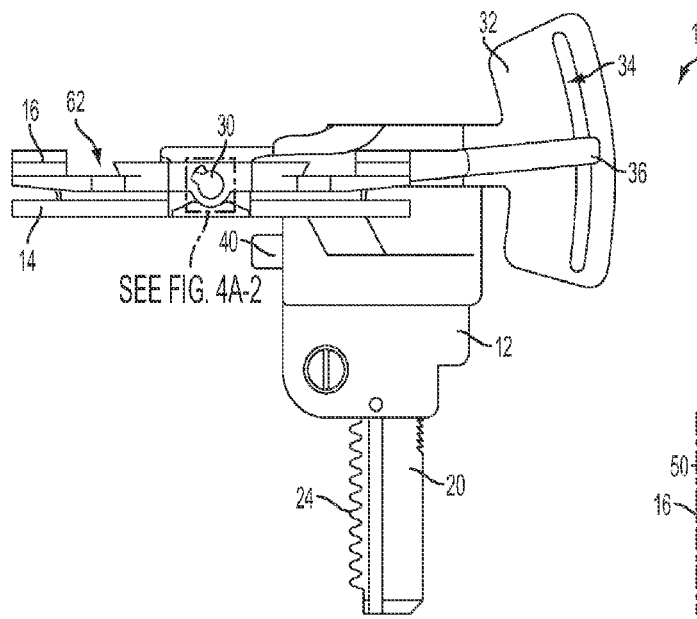
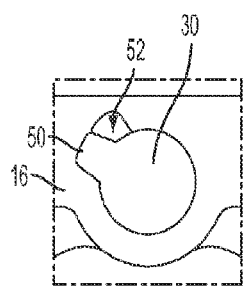
FIG. 4A-1    FIG. 4A-2
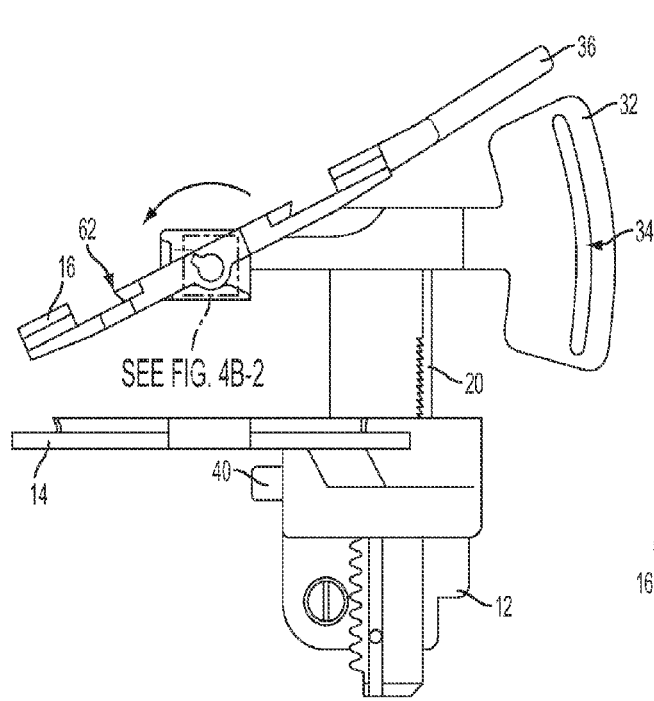
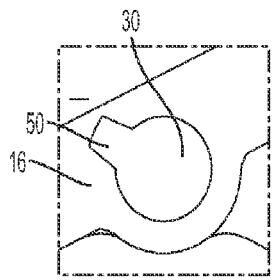
FIG. 4B-1    FIG. 4B-2

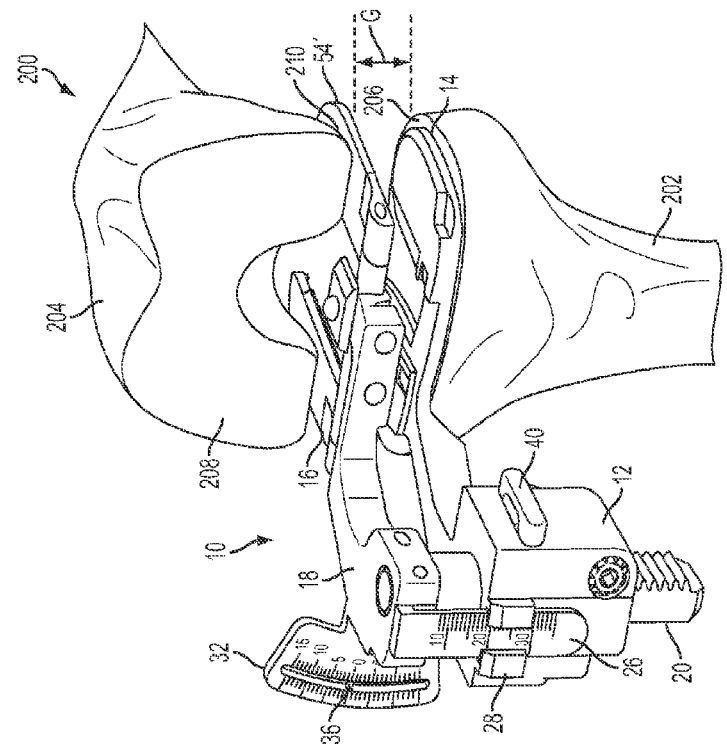

KNEE ARTHROPLASTY INSTRUMENT

CROSS REFERENCE TO RELATED APPLICATION

This application is a U.S. National Stage Filing under 35 U.S.C. 371 from International Application No. PCT/US2012/047479 filed on Jul. 19, 2012, and published as WO 2013/013094 A1, on Jan. 24, 2013, which claims priority from U.S. Provisional Patent Application Ser. No. 61/509,355, filed Jul. 19, 2011, the disclosures of which are hereby expressly incorporated by reference herein in their entireties.

FIELD OF THE DISCLOSURE

The present disclosure relates to knee arthroplasty. More particularly, the present disclosure relates to an instrument for use during a knee arthroplasty procedure, and to a method for using the same.

BACKGROUND AND SUMMARY OF THE DISCLOSURE

In a total knee arthroplasty (TKA) procedure, a patient's distal femur is resected and replaced with a prosthetic femoral implant, and the patient's proximal tibia is resected and replaced with a prosthetic tibial implant. The prosthetic femoral implant articulates with the prosthetic tibial implant to restore joint motion.

Many factors influence joint motion after the TKA procedure. The size and shape of each prosthetic implant will impact joint motion. Additionally, the location and orientation of each prosthetic implant, which is determined by the location and orientation of the corresponding bone resections, will impact joint motion. The tension or laxity of the surrounding soft tissue will also impact joint motion. For example, if the surrounding collateral ligaments are too tense, joint motion may be limited, but if the surrounding collateral ligaments are too lax, improper femoral rotation or femoral lift-off may occur. Also, the soft tissue balance around the joint will impact joint motion.

Different surgical philosophies have traditionally influenced TKA instruments and procedures. For example, a first, "measured resection" philosophy emphasizes bone resections while preserving the natural joint axis and soft tissue. A second, "soft tissue balancing" philosophy emphasizes soft tissue modifications while preserving bone.

The present invention provides an exemplary TKA instrument and procedure. The instrument separates the patient's tibia and femur, in both extension and flexion, to place the knee joint in tension and to measure a gap and an angle therebetween. The instrument includes various modular accessories. The accessories provide flexibility of usage throughout the TKA procedure. For example, the instrument may be used before resecting or otherwise manipulating the patient's knee joint to evaluate the natural knee joint and plan the TKA procedure, as well as after resecting or otherwise manipulating the patient's knee joint to evaluate and/or further plan the TKA procedure. The accessories also allow each individual user to select accessories that accommodate his or her own surgical philosophy and the needs of the particular patient. The accessories also allow the user to incorporate multiple surgical philosophies into a single surgical procedure, such as by comparing the potential outcome of one accessory with the potential outcome of another accessory.

According to an embodiment of the present invention, a knee arthroplasty instrument is provided for use in a patient's knee joint. The knee joint includes a tibia and a femur. The instrument may include a tensioning tool, a first sizer, and a second sizer different from the first sizer. The tensioning tool includes a tibial component configured for placement against the tibia and a femoral component configured for placement against the femur, the femoral component being movably coupled to the tibial component to place the patient's knee joint in tension by separating the tibia and the femur. The first sizer is removably coupled to the tensioning tool, the first sizer including at least one first reference indicator that references the femur to locate a cut guide relative to the femur. The second sizer is different from the first sizer and is removably coupled to the tensioning tool, the second sizer including at least one second reference indicator that references the femur to locate the cut guide relative to the femur.

According to another embodiment of the present invention, a knee arthroplasty instrument is provided for use in a patient's knee joint. The knee joint includes a tibia and a femur. The instrument may include a tensioning tool, a cut guide, and a sizer. The tensioning tool includes a tibial component configured for placement against the tibia and a femoral component configured for placement against the femur, the femoral component being movably coupled to the tibial component to place the patient's knee joint in tension by separating the tibia and the femur. The cut guide is removably coupled to the tensioning tool. The sizer is removably coupled to the tensioning tool to locate the cut guide relative to the femur.

According to yet another embodiment of the present invention, a knee arthroplasty method is provided for a patient's knee joint. The knee joint includes a tibia and a femur. The method may include: using a tensioning tool to place the patient's knee joint in tension by separating the tibia and the femur; selecting one of a first sizer and a second sizer, the first sizer differing from the second sizer; coupling the selected sizer to the tensioning tool; and using the selected sizer to locate a cut guide relative to the femur.

BRIEF DESCRIPTION OF THE DRAWINGS

The above-mentioned and other features and advantages of this disclosure, and the manner of attaining them, will become more apparent and the invention itself will be better understood by reference to the following description of embodiments of the invention taken in conjunction with the accompanying drawings, wherein:

FIG. 4A is a rear elevational view of the instrument of FIG. 1 showing the upper femoral component coupled to the instrument;

FIG. 4B is a rear elevational view similar to FIG. 4A showing the upper femoral component rotated for removal from the instrument;

FIG. 11A is a perspective view of the instrument positioned within the knee joint in extension, the instrument including the second, flat femoral plate of FIG. 5B;

FIG. 11B is a perspective view of the instrument positioned within the knee joint in flexion, the instrument including the second, flat femoral plate of FIG. 5B;

Corresponding reference characters indicate corresponding parts throughout the several views. The exemplifications set out herein illustrate exemplary embodiments of the invention and such exemplifications are not to be construed as limiting the scope of the invention in any manner.

DETAILED DESCRIPTION

Figure 1:
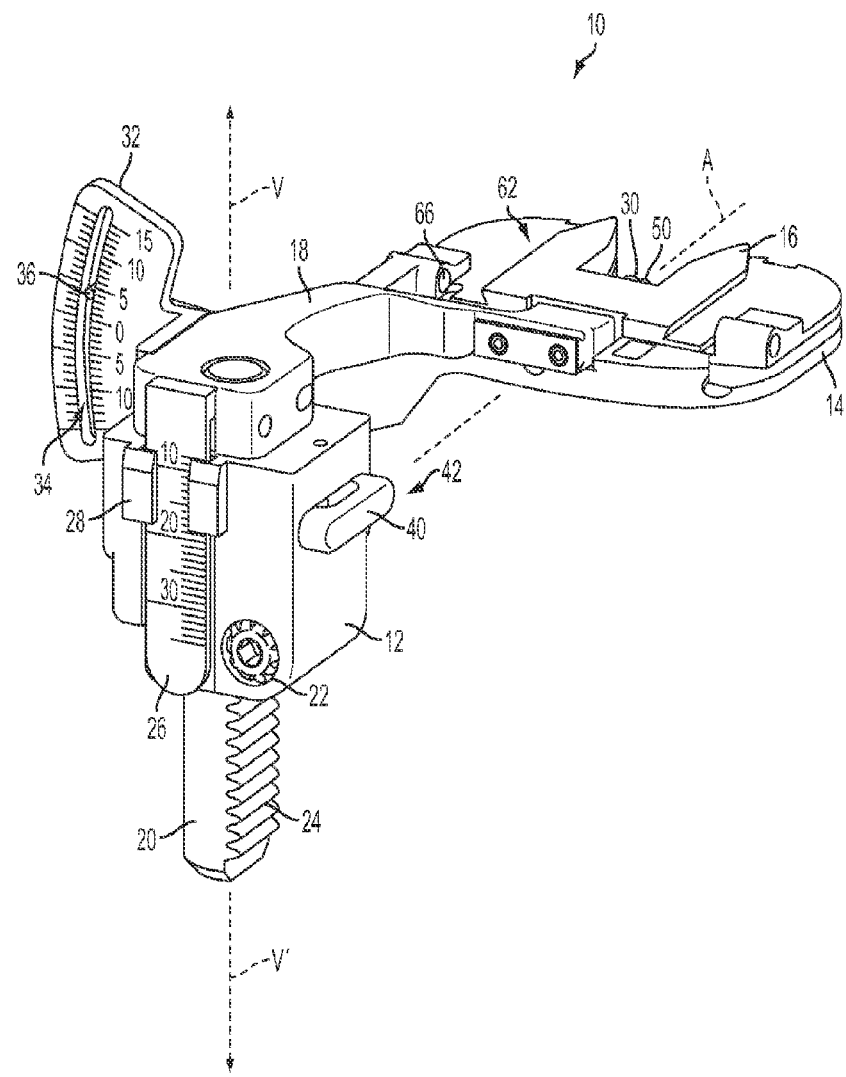
FIG. 1 is a perspective view of an exemplary tensioning instrument of the present disclosure, the instrument including a base, a lower tibial component, an upper femoral component, and an intermediate arm.
Figure 2:
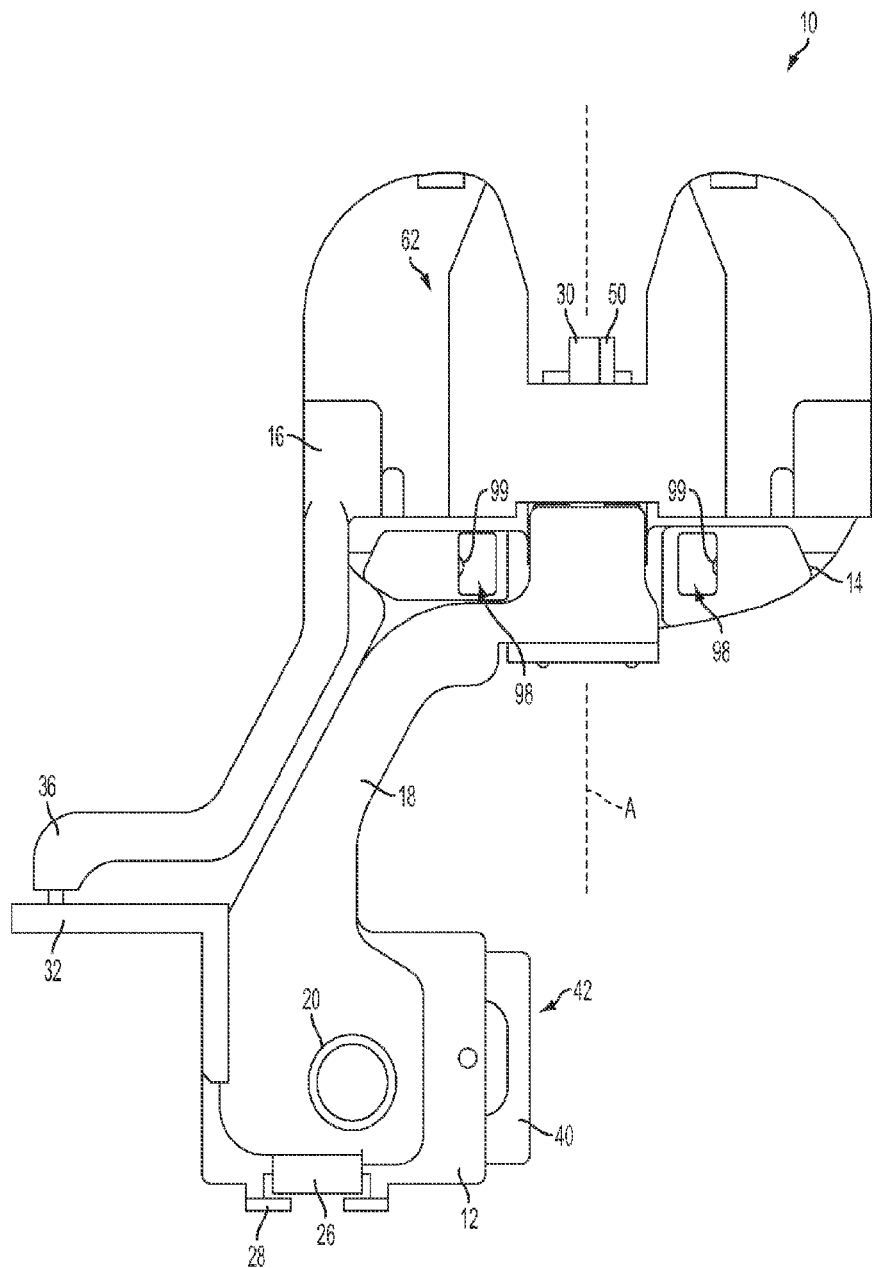
FIG. 2 is a top plan view of the instrument of FIG. 1.

With reference to FIGS. 1 and 2, a tensioning instrument 10 is provided for separating a patient's tibia and femur and measuring a joint gap and a joint angle therebetween. Instrument 10 includes a base 12, a lower tibial paddle or component 14, an upper femoral paddle or component 16, and an intermediate arm 18 that couples tibial component 14 to femoral component 16. Tibial component 14 and femoral component 16 are illustratively offset from base 12, as shown in FIG. 2, to accommodate the patient's patella. Additional information regarding instrument 10 may be found in U.S. Pat. No. 7,156,853 to Muratsu, the disclosure of which is expressly incorporated herein by reference in its entirety.

Figure 3B:
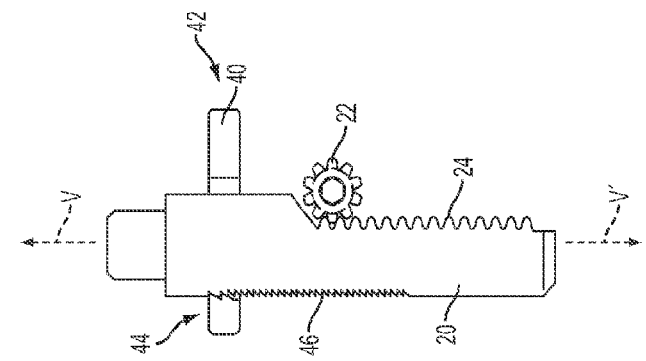
FIG. 3B is a front elevational view similar to FIG. 3A with the base, the lower tibial component, and the upper femoral component of the instrument removed to show a shaft of the intermediate arm.
Figure 3A:
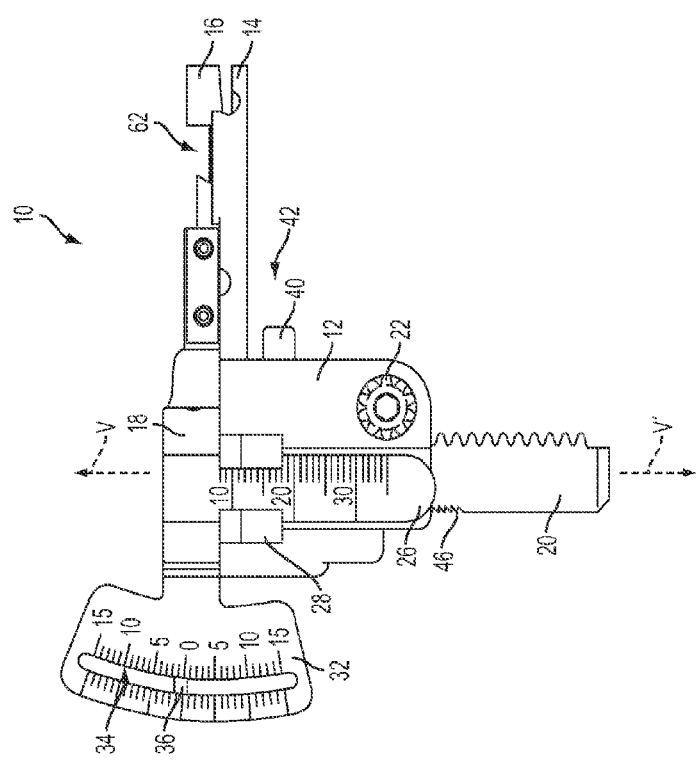
FIG. 3A is a front elevational view of the instrument of FIG. 1.

Femoral component 16 is configured to translate vertically along arrows V, V' relative to tibial component 14 via arm 18, as shown in FIG. 3A. Instrument 10 may be opened by moving femoral component 16 apart from tibial component 14 along arrow V, and instrument 10 may be closed by moving femoral component 16 toward tibial component 14 along arrow V'. As shown in FIG. 3A, arm 18 includes shaft 20 that translates vertically through base 12. Femoral component 16 is coupled to arm 18 for movement therewith relative to base 12. Shaft 20 may be keyed to base 12 to permit vertical translation of shaft 20 through base 12 while preventing rotation of shaft 20 in base 12.

A driving means is provided for selectively translating femoral component 16 relative to tibial component 14. The illustrative driving means of FIG. 3B includes a pinion gear 22 in base 12 that cooperates with a linear rack 24 on shaft 20. In use, a hex driver or another suitable tool is used to turn gear 22, and gear 22 meshes with rack 24 to drive rack 24 vertically along arrows V, V'. When opening instrument 10 along arrow V, the tool may be rotated until the patient's knee joint reaches a predetermined tension, which may occur when the user detects soft tissue resistance from the patient's knee joint to the further opening of instrument 10. In certain embodiments, instrument 10 may be opened to apply a load to the patient's knee joint of about 40 lbs., about 60 lbs., about 80 lbs., or more, although the load may vary depending on the surgeon's preference, the state of the patient's surrounding soft tissue, and other factors. It is also within the scope of the present disclosure that the tool may be torque-limited to open instrument 10 until a predetermined rotational torque of the tool is reached, wherein the predetermined rotational torque of the tool could be selected to correspond with the predetermined tension of the patient's knee joint.

A locking means is also provided to hold femoral component 16 in place relative to tibial component 14. The illustrative locking means of FIG. 3B includes a spring-biased lever 40 having an actuator end 42 and a pawl end 44. The illustrative locking means also includes a linear ratchet 46 on shaft 20 that interacts with pawl end 44 of lever 40. As shown in FIG. 3B, ratchet 46 and rack 24 are located on opposite sides of shaft 20. The locking means may allow instrument 10 to be freely opened, but the locking means may prevent instrument 10 from being closed until lever 40 is operated by the user. In the illustrated embodiment of FIG. 3B, pawl 44 permits vertically upward movement of ratchet 46 along arrow V when opening instrument 10 but resists vertically downward movement of ratchet 46 along arrow V' when closing instrument 10. When actuator end 42 of lever 40 is pressed inwardly by the user, pawl end 44 of lever 40 disengages ratchet 46, thereby permitting vertically downward movement of ratchet 46 along arrow V' to close instrument 10. Another suitable ratchet mechanism is described in the above-incorporated U.S. Pat. No. 7,156,853 to Muratsu. The locking means may also include a detent mechanism or another suitable locking mechanism, for example.

A distance measuring means is provided to measure a distance or gap G between tibial component 14 and femoral component 16 along arrows V, V'. The illustrative distance measuring means includes a distance scale 26 on arm 18 having corresponding values and a pointer 28 on base 12. As shaft 20 of arm 18 translates relative to base 12 along arrows V, V', distance scale 26 moves relative to pointer 28 on base 12. The gap G may be determined by reading the value from distance scale 26 that is aligned with the top end of pointer 28.

In addition to femoral component 16 translating vertically relative to tibial component 14, femoral component 16 is also configured to rotate relative to tibial component 14. More specifically, in addition to femoral component 16 translating vertically relative to tibial component 14 via arm 18 along arrows V, V', femoral component 16 is also configured to rotate relative to arm 18 and tibial component 14 about axis A. As shown in FIG. 2, post 30 extends into femoral component 16 from arm 18 along the rotation axis A. Femoral component 16 is configured to rotate around post 30 and rotation axis A. According to an exemplary embodiment of the present disclosure, and as shown in FIG. 1, the rotation axis A of femoral component 16 is perpendicular to the translation axes V, V' of femoral component 16.

An angle measuring means is provided to measure an angle α between tibial component 14 and femoral component 16 about the rotation axis A. The illustrative angle measuring means of FIG. 1 includes a scale plate 32 on arm 18 having corresponding values, where scale plate 32 defines an arcuate slot 34. The illustrative angle measuring means also includes a pointer 36 on femoral component 16. As femoral component 16 rotates relative to arm 18 about axis A, pointer 36 moves along or through the arcuate slot 34 of scale plate 32. The angle α may be determined by reading the value from scale plate 32 that is adjacent to pointer 36. When femoral component 16 is oriented parallel to tibial component 14, pointer 36 may be centered in slot 34 corresponding to an angle α of 0 degrees. When femoral component 16 deviates from this parallel orientation, on the other hand, pointer 36 may move along slot 34 to a positive angle α greater than 0 degrees or a negative angle α less than 0 degrees. As discussed further below, angle α may indicate a varus/valgus angle of the patient's knee joint and/or internal/external rotation of the patient's knee joint.

Instrument 10 includes a set of modular accessories, each of which is described further below. Instrument 10 and the accessories may be provided together in a kit. In this manner, a surgeon or another user may select a desired accessory from the kit and attach that first accessory to instrument 10. As the surgical procedure progresses, the user may select a second accessory from the kit and attach the second accessory to instrument 10. In certain embodiments, the first accessory may be left in place when the second accessory is attached to instrument 10. In other embodiments, the first accessory may be removed from instrument 10 to accommodate the second accessory. A variety of different coupling mechanisms (e.g., dovetail joints) and locking mechanisms (e.g., ball detents) may be used to selectively receive and retain the desired modular accessory on instrument 10, as exemplified below.

The above-described femoral component 16 may be considered a first modular accessory of instrument 10 that is removably coupled to instrument 10. As discussed above, femoral component 16 is configured to rotate around post 30 of arm 18. A tab or key 50 may be provided on post 30 to retain femoral component 16 on post 30, as shown in FIG. 4A. A keyway 52 may be provided in femoral component 16 to allow for selective removal and replacement of femoral component 16 when keyway 52 is rotated into alignment with key 50, as shown in FIG. 4B. According to an exemplary embodiment of the present disclosure, key 50 and keyway 52 are positioned such that key 50 remains offset from keyway 52 during normal rotation of femoral component 16 (e.g., 0 to 24 degrees) to resist unwanted removal of femoral component 16 during use. When removal of femoral component 16 is desired, femoral component 16 may be manually rotated beyond its normal range of motion (e.g., 25 degrees or more) to align keyway 52 with key 50.

Figure 5A:
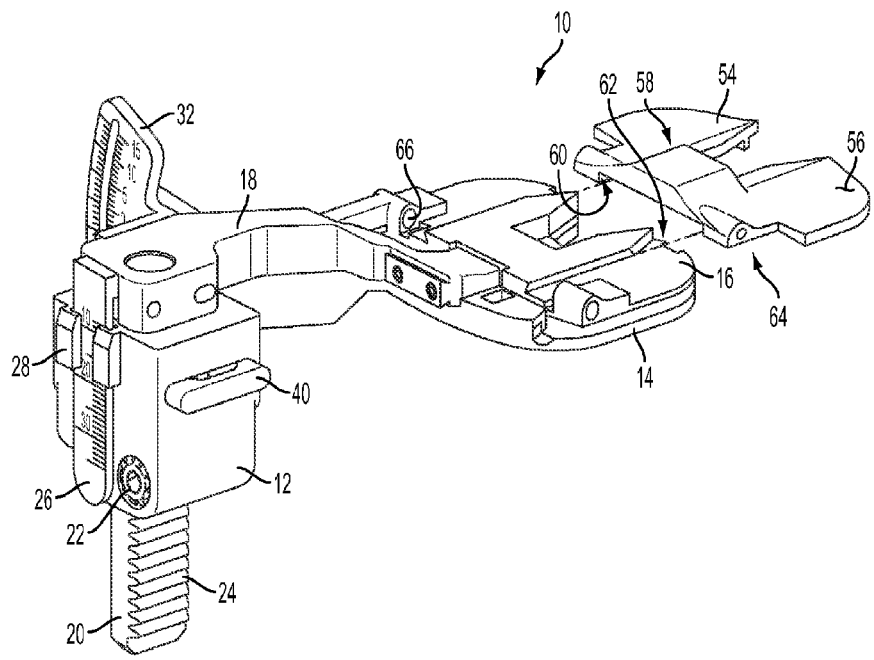
FIG. 5A is a perspective view of the instrument of FIG. 1 with a first, arcuate femoral plate.
Figure 5B:
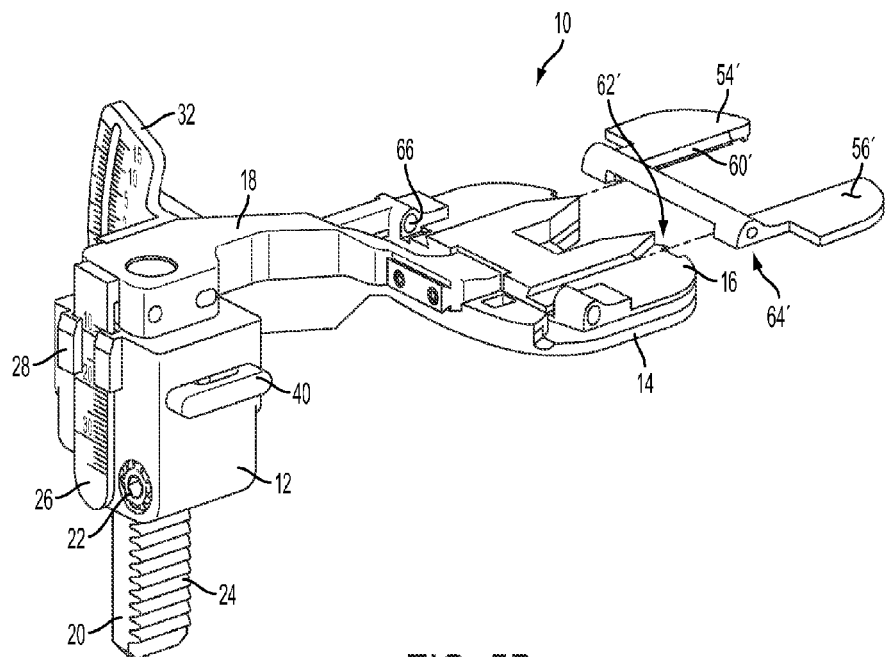
FIG. 5B is a perspective view of the instrument of FIG. 1 with a second, flat femoral plate.

Referring next to FIG. 5A, a second modular accessory of instrument 10 is provided as femoral plate 54. Femoral plate 54 includes an articular surface 56. In the illustrated embodiment of FIG. 5A, articular surface 56 of femoral plate 54 includes concave regions 58 to facilitate contact and/or articulation with convex condyles of the patient's femur. Another femoral plate 54' is shown in FIG. 5B. Femoral plate 54' of FIG. 5B is generally similar to femoral plate 54 of FIG. 5A, with like reference numerals indicating like elements, except that femoral plate 54' has a generally flat articular surface 56' to facilitate contact and/or articulation with flat, resected surfaces of the patient's femur. Femoral plates 54, 54' may be provided in different shapes and sizes for use as spacers.

Femoral plate 54 may be removably coupled to femoral component 16 of instrument 10, such that femoral plate 54 may translate vertically and rotate relative to tibial component 14 along with femoral component 16. In FIG. 5A, femoral plate 54 is attached to femoral component 16 via tongues 60 and corresponding grooves 62, where tongues 60 on femoral plate 54 are sized to slide through corresponding grooves 62 in femoral component 16. Other coupling mechanisms may also be used between femoral plate 54 and femoral component 16.

When femoral plate 54 slides into place on femoral component 16, femoral plate 54 may be selectively retained or locked in place. In FIG. 5A, femoral plate 54 may be locked onto femoral component 16 by aligning each indentation or recess 64 in femoral plate 54 with a corresponding lock 66 on femoral component 16. Each lock 66 may be in the form of a ball detent, a spring pin, or another suitable locking mechanism, for example. When removal of femoral plate 54 is desired, locks 66 may be released and freed from recesses 64 of femoral plate 54. According to an exemplary embodiment of the present disclosure, locks 66 act in a direction perpendicular to tongues 60 and grooves 62 of the coupling mechanism.

As discussed further below with reference to FIGS. 6-8, various sizers are provided as accessories of instrument 10. Exemplary sizers of the present disclosure are configured to size the patient's femur, to identify an appropriately sized femoral cut guide and an appropriately sized prosthetic femoral implant, and to locate the selected femoral cut guide and the selected femoral implant relative to the patient's femur, all with a single device. It is also within the scope of the present disclosure that the sizers may include one device to size the patient's femur and another distinct device to locate the femoral cut guide, for example.

Figure 6:
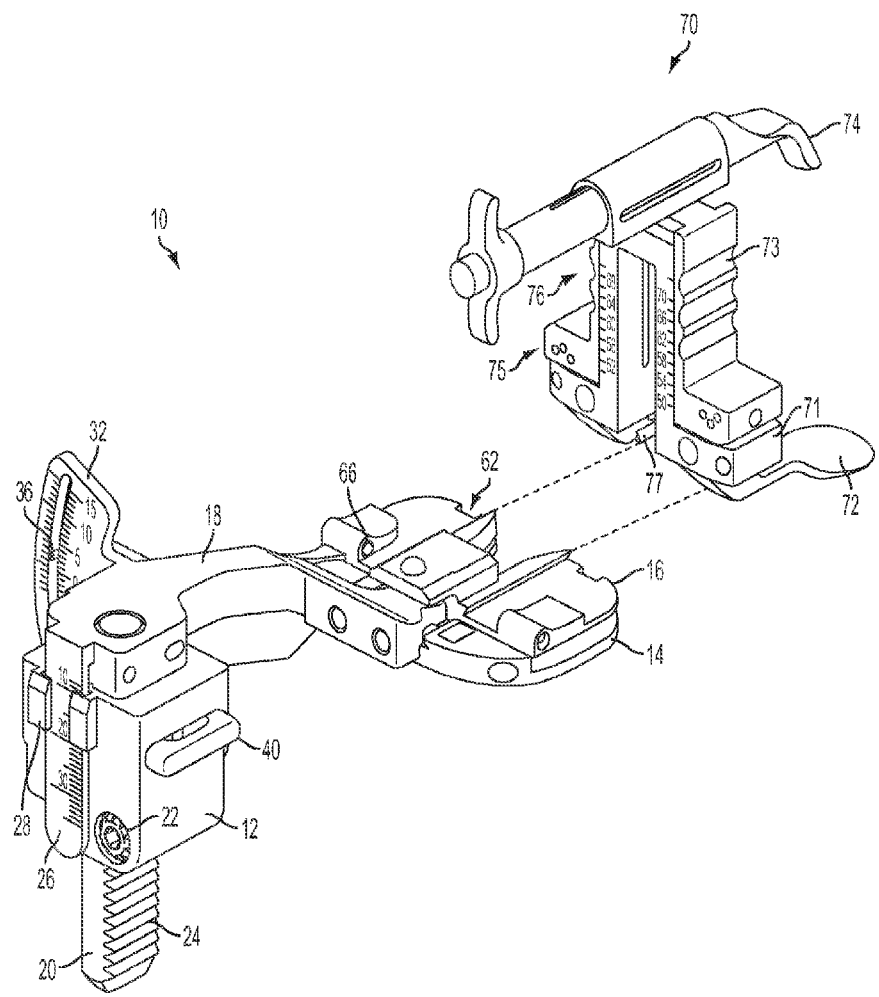
FIG. 6 is a perspective view of the instrument of FIG. 1 with a first, measured resection type sizer.

Referring next to FIG. 6, a third modular accessory of instrument 10 is provided as a measured resection type (MR-type) sizer 70. The illustrative MR-type sizer 70 includes a posterior-referencing component 71 with posterior feet 72 and an adjustable anterior-referencing component 73 with an anterior probe or stylus 74. The anterior-referencing component 73 also includes a plurality of distal-referencing indicators, illustratively holes 75. Holes 75 may be arranged in sets with each set corresponding to a desired angle of internal/external rotation, such as 0 degrees, 3 degrees, and 5 degrees of internal/external rotation. In another embodiment, bone-engaging pins may be provided in MR-type sizer 70, the pins being slidable (e.g., between holes 75) to select the desired angle of internal/external rotation.

The anterior-referencing component 73 is configured to translate vertically relative to the posterior-referencing component 71. As a result, anterior probe 74 and the distal-referencing holes 75 of the anterior-referencing component 73 translate vertically relative to posterior feet 72 of the posterior-referencing component 71. An anterior/posterior (A/P) sizing scale 76 may be provided between the adjustable anterior-referencing component 73 and the posterior-referencing component 71. More specifically, the A/P sizing scale 76 may be provided between anterior probe 74 of the adjustable anterior-referencing component 73 and posterior feet 72 of the posterior-referencing component 71. In certain embodiments, this measurement is a component size (e.g., size 12) corresponding to the separation between anterior probe 74 and posterior feet 72. In other embodiments, this measurement is the vertical distance (e.g., 60 millimeters) between anterior probe 74 and posterior feet 72. The measurement communicated by the A/P sizing scale 76 would increase as anterior probe 74 moves apart from posterior feet 72, which would also inform the user that, along with anterior probe 74, distal-referencing holes 75 have moved apart from posterior feet 72. In addition to moving vertically, anterior probe 74 is also configured to move horizontally relative to the posterior-referencing component 71 and the anterior-referencing component 73 to reference the patient's femur, as discussed further below.

The MR-type sizer 70 may be removably coupled to femoral component 16 of instrument 10, such that the MR-type sizer 70 may translate vertically and rotate relative to tibial component 14 along with femoral component 16. As a result, the distal-referencing holes 75 in the MR-type sizer 70 may also translate vertically and rotate relative to tibial component 14. According to an exemplary embodiment of the present disclosure, the MR-type sizer 70 is attached to and selectively locked onto femoral component 16 in the same manner as the above-described femoral plate 54 (FIG. 5A). For example, the MR-type sizer 70 may include tongues 77 similar to tongues 60 of femoral plate 54 for receipt in grooves 62 of femoral component 16. Also, the MR-type sizer 70 may include recesses (not shown) similar to recesses 64 of femoral plate 54 for receipt of locks 66 of femoral component 16. Other coupling mechanisms and locking mechanisms may also be used between the MR-type sizer 70 and femoral component 16.

Figure 7:
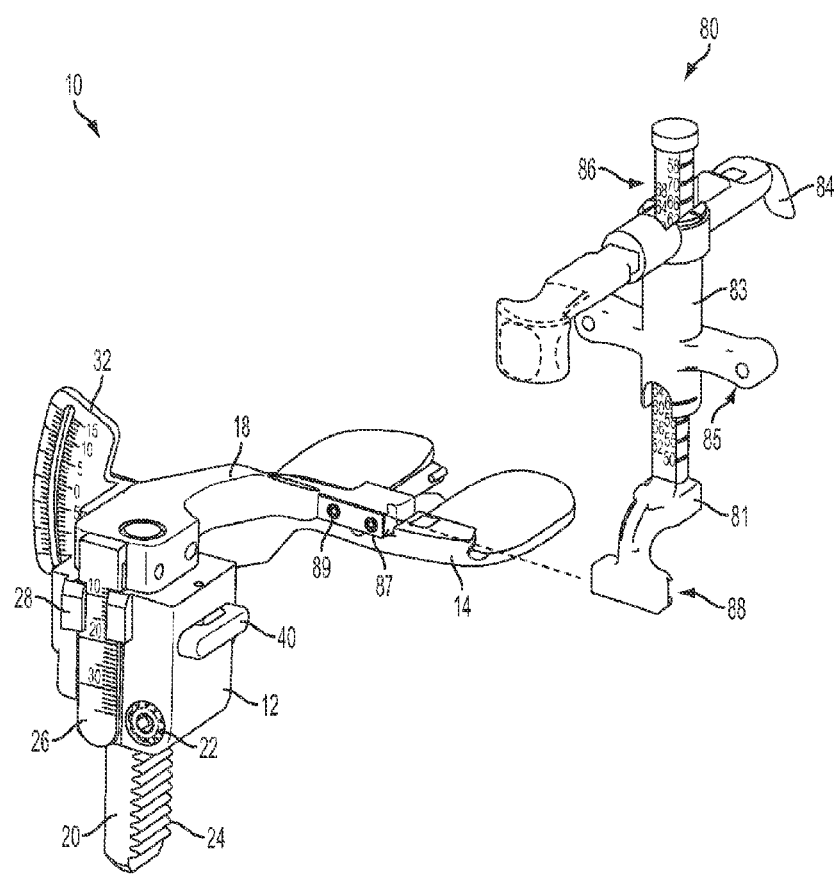
FIG. 7 is a perspective view of the instrument of FIG. 1 with a second, soft tissue balancing type sizer.

Referring next to FIG. 7, a fourth modular accessory of instrument 10 is provided as a soft tissue balancing type (STB-type) sizer 80. The STB-type sizer 80 includes a base component 81 and an adjustable anterior-referencing component 83 with an anterior probe or stylus 84. The anterior-referencing component 83 also includes a plurality of distal-referencing indicators, illustratively holes 85.

The anterior-referencing component 83 is configured to translate vertically relative to the base component 81. As a result, anterior probe 84 and the distal-referencing holes 85 of the anterior-referencing component 83 also translate vertically relative to the base component 81. An anterior/posterior (A/P) sizing scale 86 may be provided between the adjustable anterior-referencing component 83 and the base component 81. More specifically, the A/P sizing scale 86 may be provided between anterior probe 84 of the adjustable anterior-referencing component 83 and base component 81 to provide an A/P measurement between the anterior cortex and the posterior condyles. In certain embodiments, this measurement is a component size (e.g., size 12) corresponding to the separation between anterior probe 84 of the anterior-referencing component 83 and base component 81. In other embodiments, this measurement is the vertical distance (e.g., 60 millimeters) between anterior probe 84 of the anterior-referencing component 83 and base component 81. The measurement communicated by the A/P sizing scale 86 would increase as anterior probe 84 moves apart from base component 81, which would also inform the user that, along with anterior probe 84, distal-referencing holes 85 have moved apart from base component 81. In addition to moving vertically, anterior probe 84 is also configured to move horizontally relative to the base component 81 and the anterior-referencing component 83 to reference the patient's femur, as discussed further below.

The illustrative STB-type sizer 80 of FIG. 7 is an anterior-referencing sizer, with distal-referencing holes 85 translating vertically relative to base component 81 along with anterior probe 84. It is also within the scope of the present disclosure to have a posterior-referencing sizer, with distal-referencing holes 85 being vertically fixed to base component 81 and anterior probe 84 translating vertically relative to distal-referencing holes 85.

The STB-type sizer 80 may be removably coupled to arm 18 of instrument 10, such that the STB-type sizer 80 may translate vertically relative to tibial component 14 while remaining rotatably fixed relative to tibial component 14. Therefore, unlike the above-described MR-type sizer 70 (FIG. 6) that both translates vertically and rotates relative to tibial component 14, the STB-type sizer 80 may translate vertically relative to tibial component 14 without rotating relative to tibial component 14. In the illustrated embodiment of FIG. 7, the STB-type sizer 80 is attached to arm 18 via a tongue 87 and a corresponding dovetail groove 88, where tongue 87 on arm 18 is sized to slide into the corresponding groove 88 in the STB-type sizer 80. Other coupling mechanisms may also be used between the STB-type sizer 80 and arm 18.

When the STB-type sizer 80 slides onto place on arm 18, the STB-type sizer 80 may be selectively retained or locked in place. In the illustrated embodiment of FIG. 7, the STB-type sizer 80 may be locked onto arm 18 by aligning each recess (not shown) in the STB-type sizer 80 with a corresponding lock 89 in arm 18. Each lock 89 may be in the form of a ball detent, a spring pin, or another suitable locking mechanism, for example. When removal of the STB-type sizer 80 is desired, the locks 89 may be released and freed from the recesses of the STB-type sizer 80. According to an exemplary embodiment of the present disclosure, locks 89 act in a direction perpendicular to tongue 87 and groove 88 of the coupling mechanism.

Figure 8:
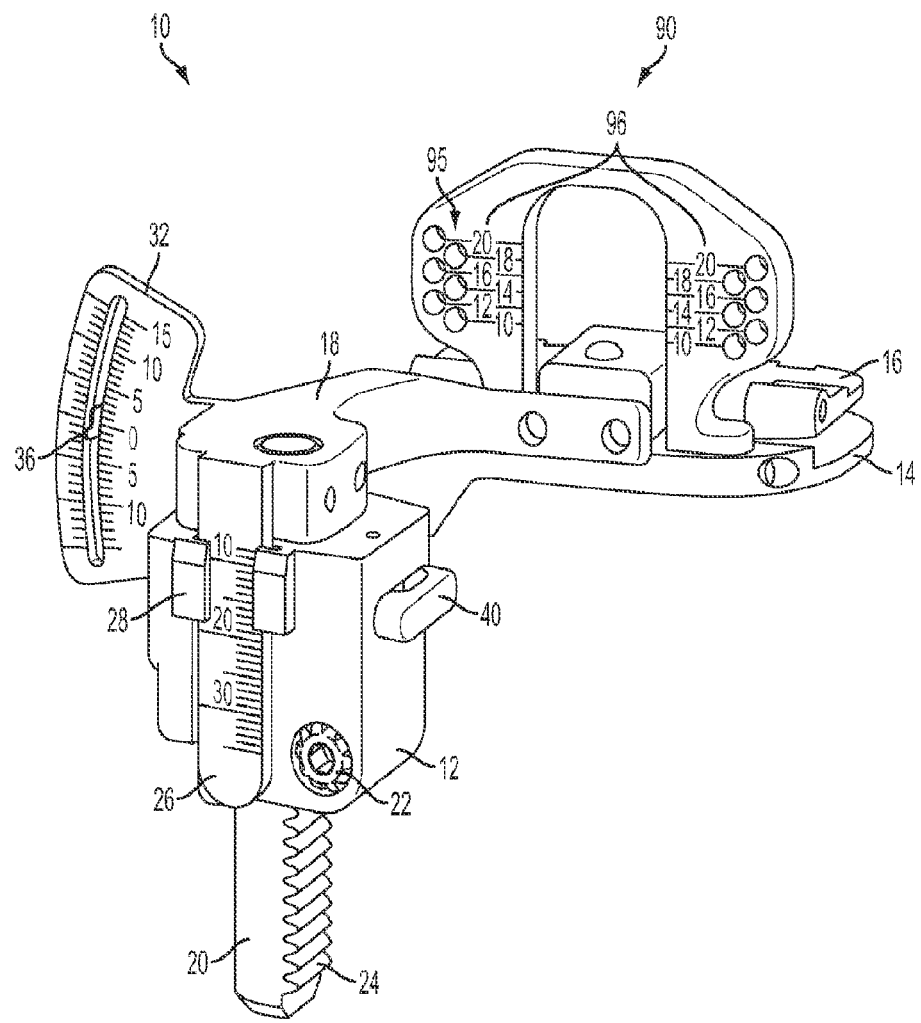
FIG. 8 is a perspective view of the instrument of FIG. 1 with a third, pure gap type sizer.

Referring next to FIG. 8, a fifth modular accessory of instrument 10 is provided as a pure gap type (PG-type) sizer 90. The PG-type sizer 90 includes a plurality of distal-referencing indicators, illustratively holes 95. Corresponding holes 95 are arranged in horizontal rows 96. In certain embodiments, each row 96 corresponds to a component size, with the row 96 closest to tibial component 14 corresponding to a relatively small component size (e.g., size 10), and the row 96 farthest from tibial component 14 corresponding to a relatively large component size (e.g., size 20). In other embodiments, each row 96 corresponds to a vertical distance from tibial component 14, with the row 96 closest to tibial component 14 corresponding to a relatively small distance, and the row 96 farthest from tibial component 14 corresponding to a relatively large distance. In this manner, rows 96 of holes 95 may serve as an A/P sizing scale of the PG-type sizer 90.

The PG-type sizer 90 may be removably coupled to tibial component 14 of instrument 10, such that the PG-type sizer 90 remains both vertically and rotatably fixed relative to tibial component 14. Therefore, unlike the above-described MR-type sizer 70 (FIG. 6), which is both rotatably and slidably coupled to tibial component 14, and the above-described STB-type sizer 80 (FIG. 7), which is slidably coupled to tibial component 14, the PG-type sizer 90 is fixedly coupled to tibial component 14. In the illustrated embodiment of FIG. 8, the PG-type sizer 90 is attached to tibial component 14 by sliding legs (not shown) on the PG-type sizer 90 into corresponding openings 98 in tibial component 14 (FIG. 2). Other coupling mechanisms may also be used between the PG-type sizer 90 and tibial component 14.

When the PG-type sizer 90 slides onto place on tibial component 14, the PG-type sizer 90 may be selectively retained or locked in place. For example, the PG-type sizer 90 may be locked onto openings 98 of tibial component 14 by aligning recesses (not shown) in the legs of the PG-type sizer 90 with corresponding locks 99 on tibial component 14 (FIG. 2). Each lock 99 may be in the form of a ball detent, a spring pin, or another suitable locking mechanism, for example. When removal of the PG-type sizer 90 is desired, the locks 99 may be released and freed from the legs of the PG-type sizer 90.

Figure 9:
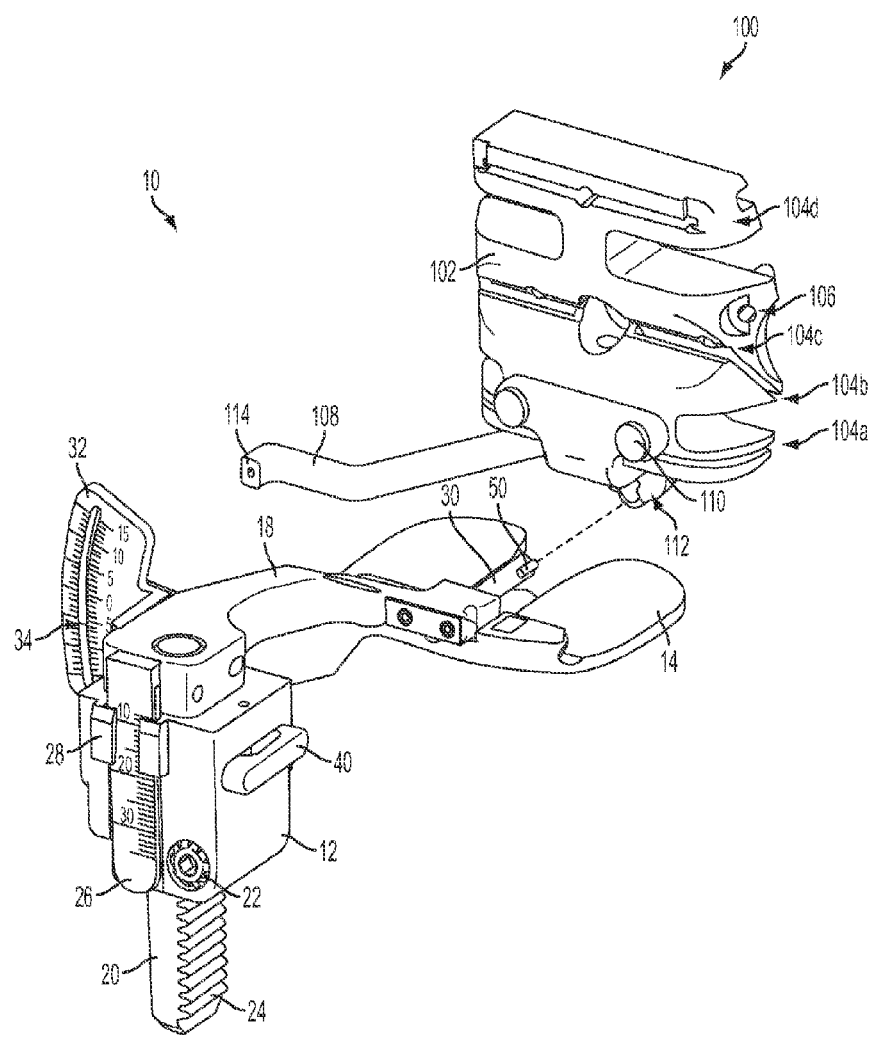
FIG. 9 is a perspective view of the instrument of FIG. 1 with a femoral cut guide.

Referring next to FIG. 9, a sixth modular accessory of instrument 10 is provided as a femoral cut guide 100. Cut guide 100 includes body 102 that defines a plurality of cut slots, illustratively a posterior cut slot 104a, a posterior chamfer cut slot 104b, an anterior chamfer cut slot 104c, and an anterior cut slot 104d. The posterior chamfer cut slot 104b and the anterior chamfer cut slot 104c may extend in opposite directions from the same opening. Because body 102 of cut guide 100 includes four (4) cut slots in FIG. 9, cut guide 100 may be referred to as a "4-in-1 cut guide." Body 102 of cut guide 100 also defines a plurality of fixation holes 106. In one exemplification, cut guide 100 further includes a connector piece 108. Connector piece 108 is illustratively removably coupled to body 102 via pegs 110, which allows body 102 to be separated from connector piece 108 during cutting. It is also within the scope of the present disclosure that connector piece 108 may be integrally formed with body 102.

Cut guide 100 may be removably coupled to and selectively locked onto arm 18 of instrument 10 in a manner similar to the above-described femoral component 16. Femoral component 16 and cut guide 100 may be interchangeably connected to instrument 10, requiring removal of one accessory (e.g., femoral component 16) to accommodate the other accessory (e.g., cut guide 100). In the illustrated embodiment of FIG. 9, for example, connector piece 108 of cut guide 100 is sized and shaped to rotate around post 30 of arm 18 in the same manner as femoral component 16. Therefore, like femoral component 16, cut guide 100 may translate vertically relative to tibial component 14 via shaft 20 of arm 18 and may also rotate relative to tibial component 14 about post 30 of arm 18. Connector piece 108 of cut guide 100 may also include a keyway 112 that is similar to keyway 52 of femoral component 16 (FIG. 4B) to allow for selective removal and replacement of cut guide 100 when keyway 112 is rotated into alignment with key 50 on post 30.

When cut guide 100 is coupled to instrument 10, the user may refer to the same distance measuring means and angle measuring means that were described above with respect to femoral component 16. For example, to measure the gap G between tibial component 14 and cut guide 100, the user may refer to distance scale 26 on shaft 20 and pointer 28 on base 12. Also, to measure the angle α between tibial component 14 and cut guide 100 about post 30, the user may refer to scale plate 32 on arm 18 and pointer 114 on connector piece 108, with pointer 114 on connector piece 108 being similar to pointer 36 on femoral component 16 (FIG. 2).

A method of using instrument 10 and its accessories will now be described with reference to FIGS. 10A-15. The ordering of the following steps may vary depending on the surgeon's preference, the patient's bone quality, the state of the patient's surrounding soft tissue, the types of prosthetic implants being used, and other factors, for example.

First, the user may perform pre-operative planning. The planning step may involve taking X-rays or other images of the patient's knee joint 200 and selecting prosthetic implants to accommodate the patient's needs, for example.

Figure 10A:
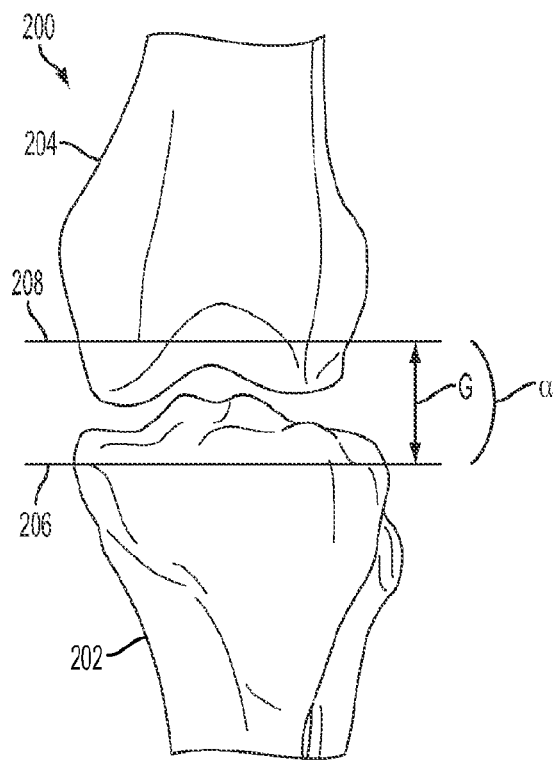
FIG. 10A is an anterior elevational view of a knee joint in extension.
Figure 10B:
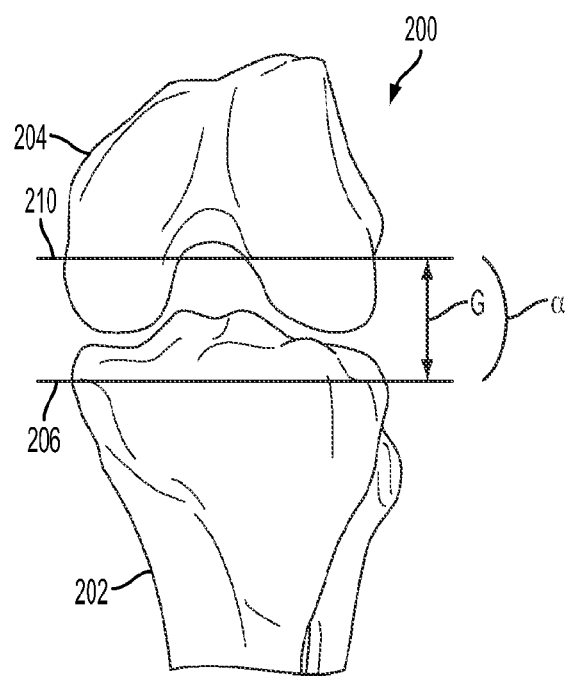
FIG. 10B is an anterior elevational view of the knee joint in flexion.

Next, as shown in FIGS. 10A and 10B, the user exposes tibia 202 and femur 204 of the patient's knee joint 200. The exposing step may involve incising the patient's skin, incising the patient's joint capsule, and removing osteophytes, for example.

With the patient's knee joint 200 now exposed, the user uses instrument 10 to separate tibia 202 and femur 204 of the patient's knee joint 200 to a predetermined tension, and to plan and identify the desired bone resections of tibia 202 and femur 204. With the patient's knee joint 200 tensioned in extension (FIG. 10A), the user is able to plan and identify a proximal tibial resection 206 and a distal femoral resection 208 that will produce a desired gap G and angle α therebetween. The extension angle α may be referred to as a varus/valgus angle. With the patient's knee joint 200 tensioned in flexion (FIG. 10B), the user is able to plan and identify the proximal tibial resection 206 and a posterior femoral resection 210 that will produce a desired gap G and angle α therebetween. The flexion angle α may be referred to as an internal/external rotation angle. Gap G and angle α between tibia 202 and femur 204 may be selected based on the patient's age, the patient's bone quality, the state of the patient's surrounding soft tissue, the types of prosthetic implants being used, and other factors, for example.

Tibia 202 and femur 204 may be resected using suitable cut guides. For example, the Minimally Invasive Surgery (MIS) Tibial Cut Guide Assembly, which is available from Zimmer, Inc. of Warsaw, Ind., may be used to form the proximal tibial resection 206 in tibia 202. Suitable cut guides may also be used to form the distal femoral resection 208 and the posterior femoral resection 210 in femur 204.

In addition to evaluating bone resections, the user may also evaluate soft tissue resections, releases, or other soft tissue operations that would impact gap G and angle α between tibia 202 and femur 204. For example, if the surgeon desires a balanced angle α of 0 degrees between tibia 202 and femur 204, the surgeon may release or otherwise relax ligaments on one side of the patient's knee joint 200 (e.g., the medial side) relative to the other side of the patient's knee joint 200 (e.g., the lateral side). As another example, if the surgeon desires a larger gap G between tibia 202 and femur 204 without resecting more bone from tibia 202 or femur 204, the surgeon may release or otherwise relax ligaments around the patient's knee joint 200.

According to an exemplary embodiment of the present disclosure, knee joint 200 is prepared such that gap G and angle α between tibia 202 and femur 204 are the same or substantially the same in extension (FIG. 10A) as in flexion (FIG. 10B). In this embodiment, a three-dimensional space may be maintained between tibia 202 and femur 204 in extension and flexion. For example, a surgeon implanting a prosthetic femoral implant having equally thick distal and femoral condyles may prepare an extension gap G that is the same as the flexion gap G, while a surgeon implanting a prosthetic femoral implant having distal and femoral condyles of different thicknesses may prepare an extension gap G that is not the exactly same as the flexion gap G to account for the different thicknesses. When angle α is 0 degrees, such that the proximal tibial resection 206 is parallel to the distal femoral resection 208 in extension (FIG. 10A) and the posterior femoral resection 210 in flexion (FIG. 10B), the three-dimensional space between tibia 202 and femur 204 will be rectangular in shape in extension and flexion. It is also within the scope of the present disclosure that the user may tolerate differences between the extension angle α (FIG. 10A) and the flexion angle α (FIG. 10B), such as differences of 1 degree, 2 degrees, or 3 degrees.

Instrument 10 may be used to separate tibia 202 and femur 204 of the patient's knee joint 200 to a predetermined tension, and to measure gap G and angle α therebetween, in both extension and flexion. Before resecting or otherwise manipulating knee joint 200, instrument 10 may be used to measure the natural gap G and angle α between tibia 202 and femur 204 in tension. Also, instrument 10 may be used to plan or identify the proximal tibial resection 206, the distal femoral resection 208, the posterior femoral resection 210, and/or any soft tissue resections that will produce a desired gap G and angle α between tibia 202 and femur 204 in tension. After resecting or otherwise manipulating knee joint 200, instrument 10 may be used to verify the desired gap G and angle α between tibia 202 and femur 204 in tension. Therefore, instrument 10 and its accessories may be used before and/or after resecting or otherwise manipulating knee joint 200.

The use of instrument 10 to measure gap G and angle α between tibia 202 and femur 204 is described further with reference to FIGS. 11A and 11B, for example. In FIG. 11A, instrument 10 is being used with the patient's knee joint 200 in extension. The proximal tibial resection 206 has already been formed in tibia 202, and the distal femoral resection 208 has already been formed in femur 204, so instrument 10 is being used to verify the resected gap G and the resected angle α between tibia 202 and femur 204. Tibial component 14 of instrument 10 is placed against the proximal tibial resection 206. Femoral plate 54' (FIG. 5B) is coupled to femoral component 16 of instrument 10 and placed against the distal femoral resection 208. With tibial component 14 and femoral component 16 of instrument 10 opened to a predetermined tension to separate tibia 202 and femur 204, the user may measure the extension gap G between the proximal tibial resection 206 and the distal femoral resection 208 by referencing distance scale 26 on shaft 20 and pointer 28 on base 12. Also, the user may measure the extension angle α between the proximal tibial resection 206 and the distal femoral resection 208 by referencing scale plate 32 on arm 18 and pointer 36 on femoral component 16.

In FIG. 11B, instrument 10 is being used with the patient's knee joint 200 in flexion. The proximal tibial resection 206 has already been formed in tibia 202, and the posterior femoral resection 210 has already been formed in femur 204, so instrument 10 is being used to verify the resected gap G and the resected angle α between tibia 202 and femur 204. Tibial component 14 of instrument 10 is placed against the proximal tibial resection 206. Femoral plate 54' (FIG. 5B) is coupled to femoral component 16 of instrument 10 and placed against the posterior femoral resection 210. With tibial component 14 and femoral component 16 of instrument 10 opened to the predetermined tension to separate tibia 202 and femur 204, the user may verify that the flexion gap G of FIG. 11B is the same as or substantially the same as the extension gap G of FIG. 11A. Also, the user may verify that the flexion angle α of FIG. 11B is the same as or substantially the same as the extension angle α of FIG. 11A. Although FIGS. 11A and 11B show the distal femoral resection 208 and the posterior femoral resection 210 in femur 204, other resections (e.g., chamfer cuts and the anterior cut) may also exist in femur 204 when instrument 10 is in use.

If necessary, the patient's knee joint 200 may be manipulated to adjust the measured gap G and/or the measured angle α between tibia 202 and femur 204. For example, if the user determines that the flexion gap G of FIG. 11B is too small compared to the extension gap G of FIG. 11A, the user may cut a deeper posterior femoral resection 210 to increase the flexion gap G of FIG. 11B. The user may also make any necessary ligament adjustments to balance the soft tissue around knee joint 200. For example, the user may release the patient's posterior cruciate ligament (PCL), which has been shown to increase the flexion gap G relative to the extension gap G.

FIGS. 11A and 11B depict post-resection use of instrument 10, with instrument 10 being positioned against resected bone surfaces of tibia 202 and femur 204. As discussed above, instrument 10 may also be used pre-resection, with instrument 10 being positioned against natural, un-resected bone surfaces of tibia 202 and femur 204. In this pre-resection condition, instrument 10 would communicate the pre-resection gap G and the pre-resection angle α between the natural, un-resected bone surfaces in tension. The user could predict the post-resection values by combining the pre-resection values with the planned resections. For example, the user could estimate the post-resection gap G by adding the planned resection depths to the corresponding pre-resection gap G.

The surgeon may also use instrument 10 to size the patient's femur 204, to select an appropriately sized femoral cut guide (e.g., cut guide 100 of FIG. 9), and to determine the location and orientation of the femoral cut guide relative to the patient's femur 204. The location and orientation of the femoral cut guide will determine the location and orientation of subsequent femoral resections and, ultimately, the location and orientation of an appropriately sized prosthetic femoral implant corresponding to the femoral cut guide. These steps may be performed by attaching a desired sizer to instrument 10, as discussed further below. The sizer type may vary depending on the surgeon's preference, the patient's bone quality, the state of the patient's surrounding soft tissue, the type of prosthetic femoral implant being used, and other factors, for example.

Figure 12:
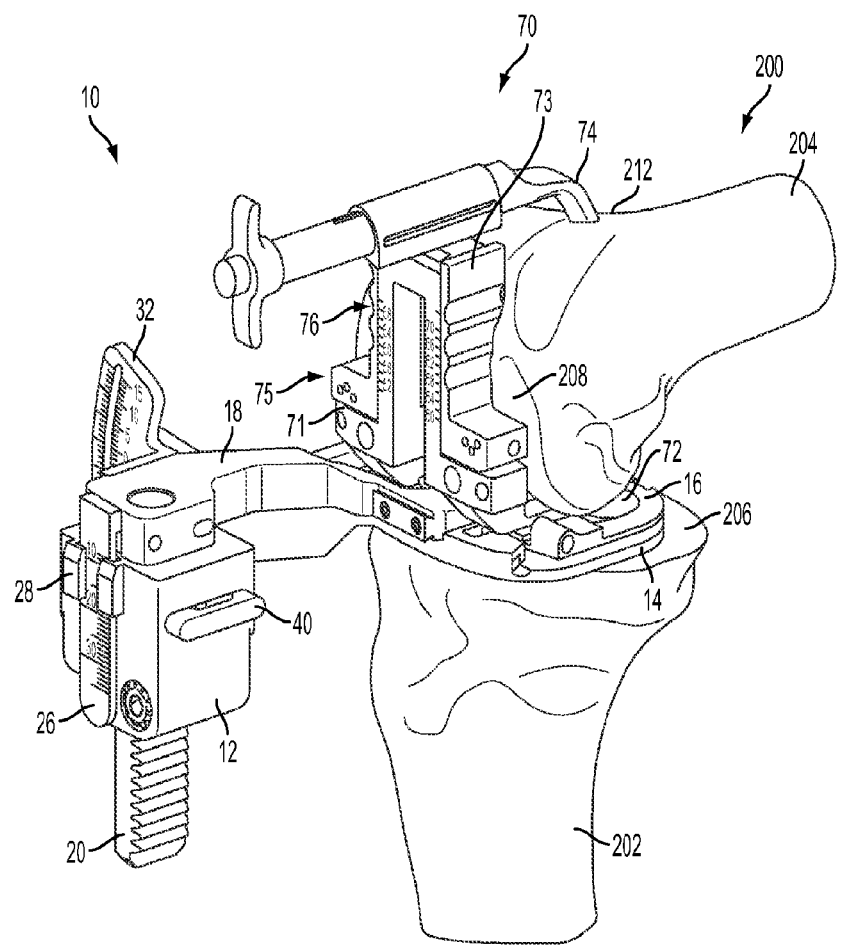
FIG. 12 is a perspective view of the instrument positioned within the knee joint in flexion, the instrument including the first, measured resection type sizer of FIG. 6.

The MR-type sizer 70 is shown attached to instrument 10 in FIG. 12 (see also FIG. 6). With the patient's knee joint 200 in flexion, tibial component 14 of instrument 10 is positioned against the patient's tibia 202, posterior feet 72 of the MR-type sizer 70 are placed against the patient's uncut posterior femur 204, and anterior probe 74 of the MR-type sizer 70 is placed against the patient's anterior femoral cortex 212. In this arrangement, the user may reference the A/P sizing scale 76 to size the patient's femur 204 and select an appropriately sized cut guide. The user may also use a set of distal-referencing holes 75 in the MR-type sizer 70 as guides to mark or drill distal fixation holes (not shown) into the patient's femur 204 for eventual receipt of the cut guide, with the selected set of distal-referencing holes 75 controlling internal/external rotation of the corresponding femoral cut guide and the corresponding prosthetic femoral implant. Because the MR-type sizer 70 is coupled to femoral component 16 of instrument 10 for rotation therewith, rotation of the patient's femur 204 on femoral component 16 will also cause rotation of the distal-referencing holes 75 in the MR-type sizer 70. As a result, the distal-referencing holes 75 may track or follow the bone of the patient's femur 204 as it rotates relative to the patient's tibia 202. In this manner, the bone of the patient's femur 204 (i.e., the "measured resections" of the patient's femur 204) will impact internal/external rotation of distal-referencing holes 75, as well as the placement of the corresponding femoral cut guide and the corresponding prosthetic femoral implant.

Figure 13:
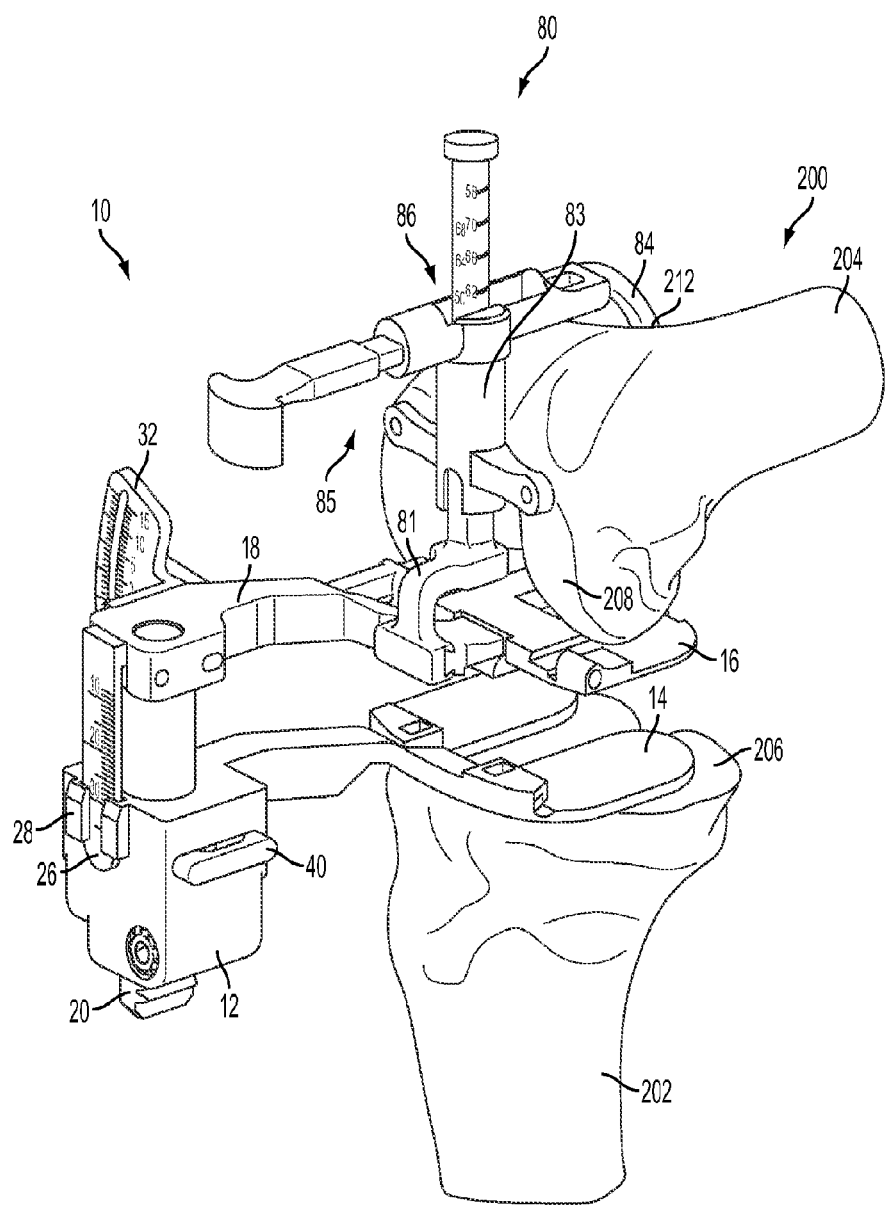
FIG. 13 is a perspective view of the instrument positioned within the knee joint in flexion, the instrument including the second, soft tissue balancing type sizer of FIG. 7.

The STB-type sizer 80 is shown attached to instrument 10 in FIG. 13 (see also FIG. 7). With the patient's knee joint 200 in flexion, tibial component 14 of instrument 10 is positioned against the patient's tibia 202, femoral component 16 of instrument 10 is placed against the patient's uncut posterior femur 204, and anterior probe 84 of the STB-type sizer 80 is placed against the patient's anterior femoral cortex 212. Although FIG. 13 shows femoral component 16 of instrument 10 in contact with the patient's posterior femur 204, one of femoral plate 54 and femoral plate 54' will be attached to femoral component 16 of instrument 10 to directly contact the patient's posterior femur 204. In these arrangements, the user may reference the A/P sizing scale 86 to size the patient's femur 204 and select an appropriately sized cut guide. The user may also use the distal-referencing holes 85 in the STB-type sizer 80 as guides to mark or drill distal fixation holes (not shown) into the patient's femur 204 for eventual receipt of the cut guide. Because the STB-type sizer 80 is not rotatable relative to tibial component 14 of instrument 10, rotation of the patient's femur 204 on femoral component 16 will not rotate the STB-type sizer 80. As a result, the distal-referencing holes 85 may remain rotatably fixed in space, even as soft tissue of the knee joint 200 causes the patient's femur 204 to rotate relative to the patient's tibia 202 as the joint is placed in tension. In this manner, "soft tissue balancing" around the patient's femur 204 will impact internal/external rotation of distal-referencing holes 85 relative to the patient's femur 204, as well as the placement of the corresponding femoral cut guide and the corresponding prosthetic femoral implant.

Figure 14:
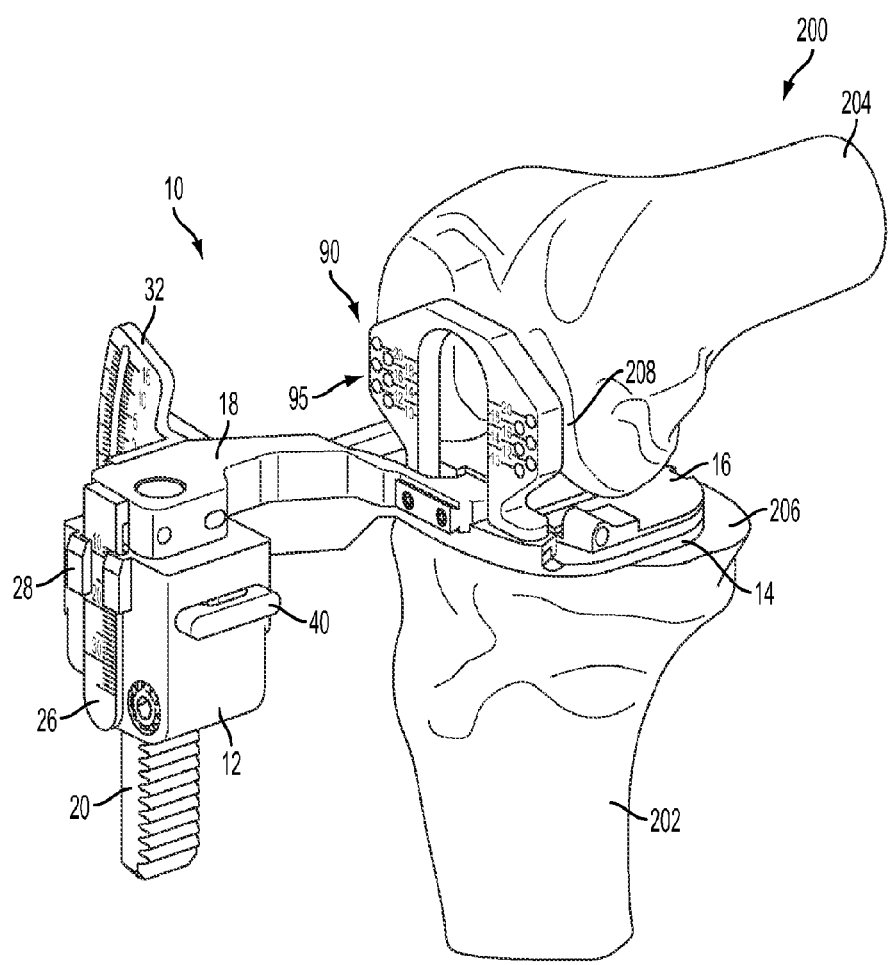
FIG. 14 is a perspective view of the instrument positioned within the knee joint in flexion, the instrument including the third, pure gap type sizer of FIG. 8.

The PG-type sizer 90 is shown attached to instrument 10 in FIG. 14 (see also FIG. 8). With the patient's knee joint 200 in flexion, tibial component 14 of instrument 10 is positioned against the patient's tibia 202, and femoral component 16 of instrument 10 is placed against the patient's uncut posterior femur 204. Although FIG. 14 shows femoral component 16 of instrument 10 in contact with the patient's posterior femur 204, one of femoral plate 54 and femoral plate 54' will be attached to femoral component 16 of instrument 10 to directly contact the patient's posterior femur 204. The patient's knee joint 200 may also be moved to extension with the PG-type sizer 90.

Based on the size of the patient's femur 204 and the gap G produced when the patient's knee joint 200 is tensioned in flexion and/or extension, the user may identify an appropriate row 96 of distal-referencing holes 95 in the PG-type sizer 90 and select the corresponding cut guide. For example, after forming the distal femoral resection 208 in femur 204, the user may measure the extension gap G produced when the patient's knee joint 200 is tensioned in extension. Then, the user may tension the patient's knee joint 200 in flexion to the same tension as in extension and select the row 96 of distal-referencing holes 95 in the PG-type sizer 90 that correspond to the previously-measured extension gap G. The user may then use the selected distal-referencing holes 95 in the PG-type sizer 90 as guides to mark or drill distal fixation holes (not shown) into the patient's femur 204 for eventual receipt of the cut guide, thereby arriving at a posterior femoral resection 210 (FIG. 10B) that produces the same flexion gap G as the previously-measured extension gap G. Because the PG-type sizer 90 is coupled to tibial component 14 of instrument 10, rotation or translation of the patient's femur 204 on femoral component 16 will not rotate or translate the PG-type sizer 90. As a result, the distal-referencing holes 95 may remain fixed in space, even as soft tissue of the knee joint 200 causes the patient's femur 204 to rotate or translate relative to the patient's tibia 202 as the joint is placed in tension. In this manner, soft tissue around the patient's femur 204 will impact internal/external rotation of distal-referencing holes 95 relative to the patient's femur 204, as well as the placement of the corresponding femoral cut guide and the corresponding prosthetic femoral implant.

In certain embodiments, the user may interchangeably couple more than one sizer 70, 80, 90 to instrument 10 during a single surgical procedure and compare the potential outcomes of each sizer 70, 80, 90 in that surgical procedure. For example, the user may compare the planned location and orientation of distal-referencing holes 75, 85, 95, for each sizer 70, 80, 90, and then continue with a desired sizer 70, 80, 90.

Figure 15:
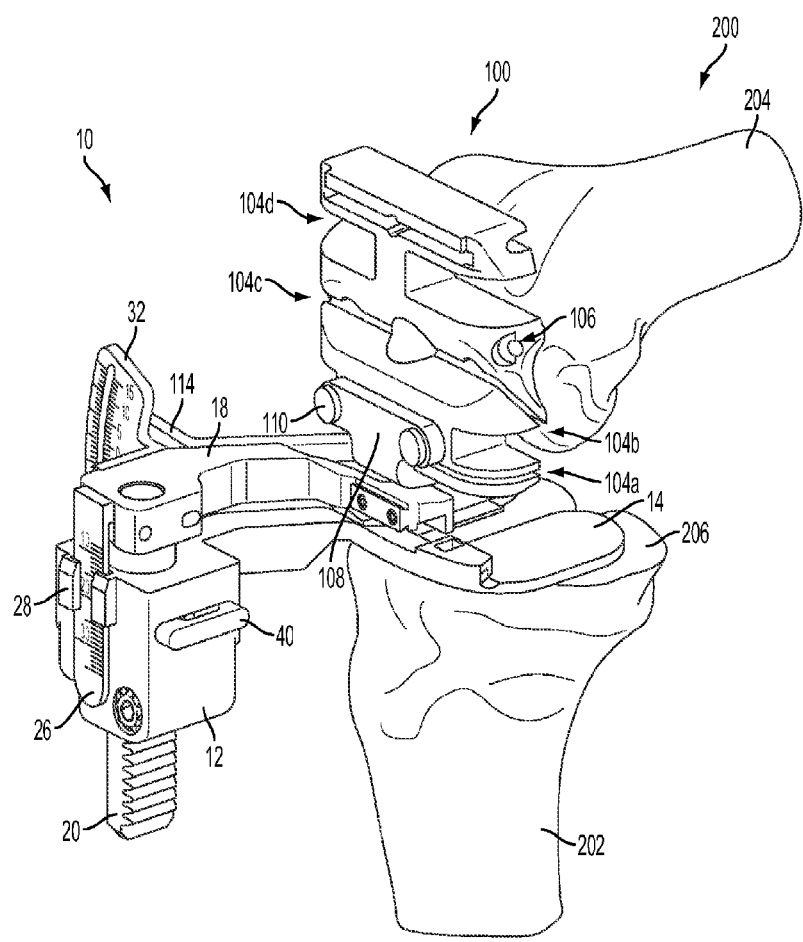
FIG. 15 is a perspective view of the instrument positioned within the knee joint in flexion, the instrument including the femoral cut guide of FIG. 9.

After using instrument 10 to mark or drill distal fixation holes (not shown) into the patient's femur 204, the user uses instrument 10 in FIG. 15 to confirm the location and orientation of the selected cut guide 100. Cut guide 100 is illustratively coupled to instrument 10 via connector piece 108, as discussed further above with respect to FIG. 9. During this confirming step, the user may visually or otherwise align fixation holes 106 in cut guide 100 with the pre-marked or pre-drilled distal fixation holes on the patient's distal femur 204. If the markings are in the form of symbols (e.g., circles, crosses) drawn onto the patient's distal femur 204, for example, fixation holes 106 in cut guide 100 may be visually aligned with the symbols to overlap the symbols. If the markings are in the form of pins or other reference structures extending from the patient's distal femur 204, fixation holes 106 in cut guide 100 may be placed onto the pins. In such arrangements, the user may verify the location and orientation of cut guide 100 relative to the patient's femur 204. More specifically, the user may verify the location and orientation of cut slots 104a, 104b, 104c, 104d, relative to the patient's femur 204. When cut guide 100 is attached to instrument 10, the user may also use instrument 10 to verify gap G and angle α between tibia 202 and femur 204.

Advantageously, before cutting the patient's bone, instrument 10 enables the user to adjust the location and/or orientation of cut guide 100. For example, if the patient's bone stock along one or more cut slots 104a, 104b, 104c, 104d, is inadequate, the user may repeat some or all of the above-described method steps to re-evaluate and adjust the location and/or orientation of cut guide 100.

After using instrument 10 to confirm the location and orientation of cut guide 100 in FIG. 15, the user may separate connector piece 108 from body 102 and affix body 102 to the patient's femur 204. Body 102 may be affixed to the patient's femur 204 by driving supports (e.g., pins, nails, screws, or other anchors) through fixation holes 106 of body 102 and into the patient's femur 204. Based on the previous alignment step, the anchors would extend into the pre-marked or pre-drilled distal fixation holes (not shown) in the patient's femur 204.

With body 102 of cut guide 100 affixed to the patient's femur 204, the user may cut bone by drawing an oscillating saw or another suitable tool (not shown) through some or all of the cut slots 104a, 104b, 104c, 104d, in cut guide 100. If posterior femoral resection 210 was previously formed in femur 204, it may be unnecessary to use posterior cut slot 104a of cut guide 100. However, the surgeon will generally form distal femoral resection 208 in femur 204, and then form the remaining resections in femur 204 (including posterior femoral resection 210) using cut slots 104a, 104b, 104c, 104d, of cut guide 100 based on the outcome of the selected sizer 70, 80, 90.

Next, the user may temporarily secure trial implants (not shown) to the patient's resected tibia 202 and femur 204 and use instrument 10 to confirm the location and orientation of the trial implants. For example, with tibial component 14 of instrument 10 positioned against a trial tibial implant and femoral component 16 of instrument 10 positioned against a trial femoral implant, the user may use instrument 10 to verify gap G and angle α therebetween.

Finally, the user may affix final prosthetic implants (not shown) to the patient's resected tibia 202 and femur 204. The final prosthetic implants may be secured in place with anchors and/or bone cement, for example. Again, the user may use instrument 10 to confirm the location and orientation of the final prosthetic implants.

While this invention has been described as having exemplary designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A knee arthroplasty instrument for use in a knee joint, the knee joint including a tibia and a femur, the instrument comprising:
    a tensioning tool including a tibial component configured for placement against the tibia and a femoral component configured for placement against the femur, the femoral component being movably coupled to the tibial component to place the knee joint in tension by separating the tibia and the femur;
    a first sizer removably coupleable to the tensioning tool, the first sizer including at least one first reference indicator that references the femur to locate a cut guide relative to the femur;
    a second sizer different from the first sizer, used in alternative to the first sizer and removably coupleable to the tensioning tool, the second sizer including at least one second reference indicator that references the femur to locate the cut guide relative to the femur; and
    a cut guide removably coupleable to the tensioning tool, wherein the femoral component of the tensioning tool and the cut guide are interchangeably coupleable to the instrument, the femoral component of the tensioning tool being separable from the instrument to accommodate the cut guide on the instrument.

2. The instrument of claim 1, wherein the first sizer is one of:
    a measured resection type sizer that translates and rotates relative to the tibial component of the tensioning tool;
    a soft tissue balancing type sizer that translates relative to the tibial component of the tensioning tool without rotation; and
    a pure gap type sizer that is fixed in space relative to the tibial component of the tensioning tool.

3. The instrument of claim 1, wherein the first sizer is removably coupleable to a first location of the tensioning tool and the second sizer is removably coupleable to a second location of the tensioning tool different from the first location.

4. The instrument of claim 1, wherein the first sizer rotates with the femoral component relative to the tibial component when the first sizer is coupled to the tensioning tool.

5. The instrument of claim 1, wherein the first sizer translates with the femoral component relative to the tibial component when the first sizer is coupled to the tensioning tool.

6. The instrument of claim 1, wherein the second sizer is rotatably fixed relative to the tibial component when the second sizer is coupled to the tensioning tool such that the femoral component rotates relative to the second sizer and the tibial component when the second sizer is coupled to the tensioning tool.

7. The instrument of claim 1, wherein the second sizer translates with the femoral component relative to the tibial component when the second sizer is coupled to the tensioning tool.

8. The instrument of claim 1, wherein the second sizer includes:
    a base component;
    a second anterior-referencing component configured to contact an anterior surface of the femur, the second anterior-referencing component including a body that is movably coupled to the base component for movement relative to a condyle of the femur and an extension that extends transversely from the body to reference an anterior cortex of the femur; and
    a second sizing scale between the base component and the second anterior-referencing component.

9. The instrument claim 1, further comprising a third sizer different from each of the first and second sizers and removably coupleable to the tensioning tool, the third sizer including at least one third reference indicator that references the femur to locate the cut guide relative to the femur.

10. The instrument of claim 9, wherein the third sizer is fixed in space relative to the tibial component when the third sizer is coupled to the tensioning tool such that the femoral component rotates and translates relative to the third sizer and the tibial component when the third sizer is coupled to the tensioning tool.

11. The instrument of claim 9, wherein the third sizer extends vertically from the tibial component without extending horizontally over the femoral component such that the third sizer lacks an anterior-referencing component, the third sizer accommodating the femur in flexion and in extension on the femoral component when the third sizer is coupled to the tensioning tool.

12. The instrument of claim 1, wherein the cut guide includes a plurality of supports that are sized and spaced to support the cut guide on the femur, wherein the first sizer includes a plurality of first reference indictors and the second sizer includes a plurality of second reference indicators, and wherein at least one of the plurality of first reference indicators of the first sizer and the plurality of second reference indicators of the second sizer is sized and spaced to locate the plurality of supports of the cut guide relative to the femur.

13. The instrument of claim 1, wherein the femoral component of the tensioning tool translates and rotates relative to the tibial component of the tensioning tool, and the cut guide translates and rotates relative to the tibial component of the tensioning tool when the cut guide is coupled to the tensioning tool.

14. A knee arthroplasty instrument for use in a knee joint, the knee joint including a tibia and a femur, the instrument comprising:
    a tensioning tool including a tibial component configured for placement against the tibia and a femoral component configured for placement against the femur, the femoral component being movably coupled to the tibial component to place the knee joint in tension by separating the tibia and the femur;
    a first sizer removably coupleable to the tensioning tool, the first sizer including at least one first reference indicator that references the femur to locate a cut guide relative to the femur; and
    a second sizer different from the first sizer and removably coupleable to the tensioning tool, the second sizer including at least one second reference indicator that references the femur to locate the cut guide relative to the femur;

wherein the first sizer includes:

a first posterior-referencing component that is configured to contact a posterior surface of the femur;

a first anterior-referencing component that is configured to contact an anterior surface of the femur, the first anterior-referencing component including a body that is movably coupled to the first posterior-referencing component for movement relative to a condyle of the femur and an extension that extends transversely from the body to reference an anterior cortex of the femur; and a first sizing scale between the first posterior-referencing component and the first anterior-referencing component.

15. A knee arthroplasty instrument for use in a knee joint, the knee joint including a tibia and a femur, the instrument comprising:

a tensioning tool including a tibial component configured for placement against the tibia and a femoral component configured for placement against the femur, the femoral component being movably coupled to the tibial component to place the knee joint in tension by separating the tibia and the femur;

a first sizer removably coupleable to the tensioning tool, the first sizer including at least one first reference indicator that references the femur to locate a cut guide relative to the femur;

a second sizer different from the first sizer, used in alternative to the first sizer and removably coupleable to the tensioning tool, the second sizer including at least one second reference indicator that references the femur to locate the cut guide relative to the femur; and a cut guide removably coupleable to the tensioning tool, wherein the femoral component of the tensioning tool and the cut guide are each individually:

retained on the instrument by a key; and removed from the instrument by rotating a keyway into alignment with the key.

* * * * *

UNITED STATES PATENT AND TRADEMARK OFFICE
CERTIFICATE OF CORRECTION

PATENT NO. : 10,166,034 B2  
APPLICATION NO. : 14/233227  
DATED : January 1, 2019  
INVENTOR(S) : Claypool et al.

Page 1 of 1

It is certified that error appears in the above-identified patent and that said Letters Patent is hereby corrected as shown below:

In the Claims

In Column 16, Line 21, in Claim 9, after "instrument", insert --of--

In Column 16, Line 41, in Claim 12, delete "indictors" and insert --indicators-- therefor Signed and Sealed this
Twenty-first Day of April, 2020

Andrei Iancu
*Director of the United States Patent and Trademark Office*